United States Patent [19]

Klein et al.

[11] Patent Number: 4,624,742

[45] Date of Patent: Nov. 25, 1986

[54] METHOD OF DETERMINING BLACK LIQUOR SOLIDS CONCENTRATION REMAINING IN A WASHED PULP MAT

[75] Inventors: Edward P. Klein; Thomas M. Neider, both of Covington, Va.

[73] Assignee: Westvaco Corporation, New York, N.Y.

[21] Appl. No.: 583,988

[22] Filed: Feb. 27, 1984

[51] Int. Cl.[4] .......................... D21C 9/02; D21C 9/06
[52] U.S. Cl. ..................................... 162/49; 68/13 R; 162/60; 162/263; 210/746; 210/104
[58] Field of Search .................. 162/49, 263, 60, 262, 162/DIG. 10, 198, 61, 62; 210/246, 86, 96.1, 104; 68/13 R; 324/61 R

[56] References Cited

U.S. PATENT DOCUMENTS 4,046,621 9/1977 Sexton ................................. 162/49
4,096,028 6/1978 Rosenberger ...................... 162/60
4,207,141 6/1980 Seymour ............................. 162/60

OTHER PUBLICATIONS

Gossage et al, "Correlation of Solids & Soda Content with Conductivity in Brown Stock Washer Systems"; *TAPPI*, vol. 60,4, Apr. 1977, p. 110.
Gulley, "Filtrate Conductivity Can Give Misleading Indications of Washer Loses"; *TAPPI*, Mar. 1980, vol. 63, No. 3, p. 33.

*Primary Examiner*—Steve Alvo
*Attorney, Agent, or Firm*—W. A. Marcontell; R. L. Schmalz

[57] ABSTRACT

A method and apparatus is provided for measuring the present and ongoing performance of paper pulp brown stock washers. Black liquor carryover within a washer mat past wash liquor application showers is quantified by determination of and correlation with the mat liquor specific conductivity.

3 Claims, 6 Drawing Figures

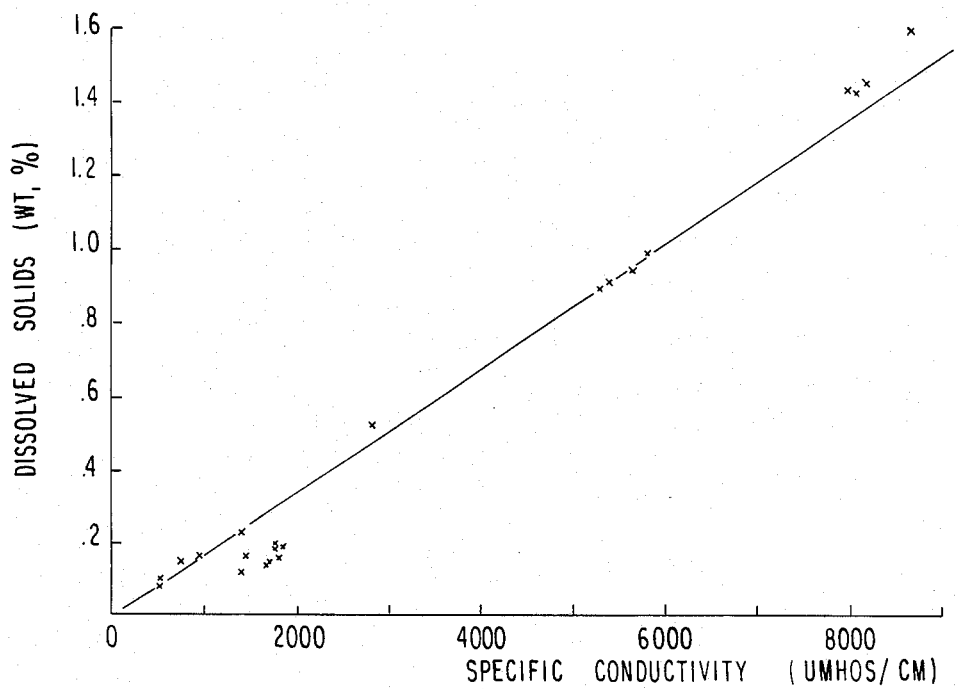
FIG. 3 MAT LIQUOR DISSOLVED SOLIDS VS. LIQUOR CONDUCTIVITY (PINE)
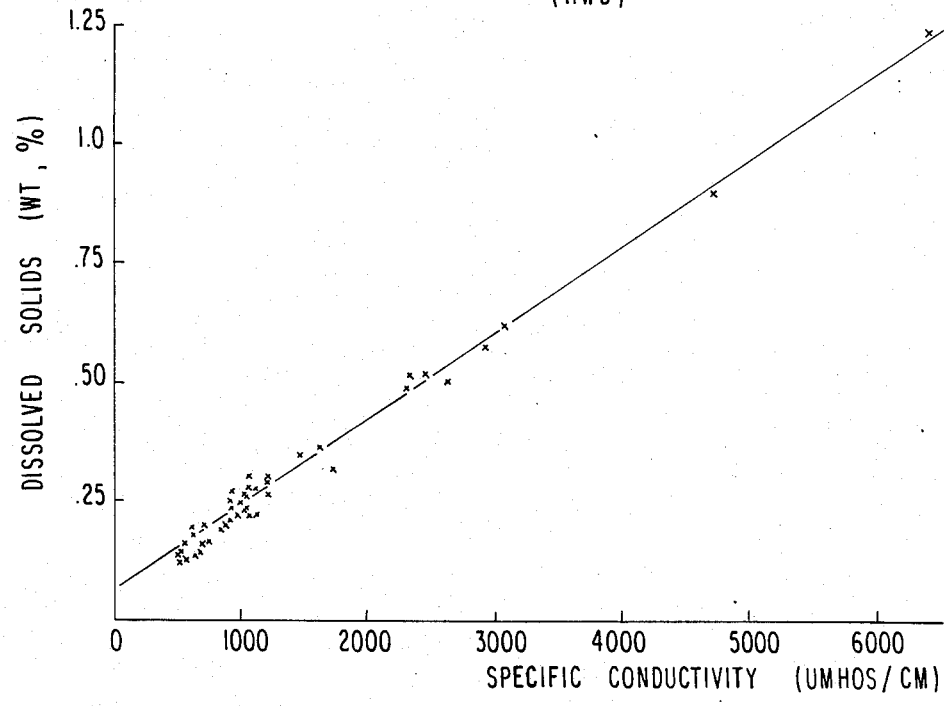
FIG. 4 MAT LIQUOR DISSOLVED SOLIDS VS. LIQUOR CONDUCTIVITY (HWD)

METHOD OF DETERMINING BLACK LIQUOR SOLIDS CONCENTRATION REMAINING IN A WASHED PULP MAT

BACKGROUND OF THE INVENTION

1. Field of the Invention

The present invention relates to the preparation of cellulose fiber pulp from wood and other cellulosic materials. More particularly, the present invention relates to a method and apparatus for continuously monitoring the quantity of dissolved solids remaining in the interstices of a brown pulp stock mat carried by a wash filter surface.

2. Description of the Prior Art

Raw wood, bagasse and other cellulosic fiber sources are delignified by cooking processes in the presence of chemicals which form water soluble compounds and complexes with the natural lignin binder of the raw fiber matrix. Although the chemicals used in the digestive cooking process are relatively inexpensive, those quantities consumed in the 1500 tons of dry pulp per day production of an average pulp mill necessitates an economical recovery and recycle of such chemical values. Moreover, the lignin compounds which must be removed from the cellulose fiber matrix contain sufficient heat value and volatility to contribute favorably to the overall mill heat balance.

The objectives of chemical and heat value recovery from wood cooking liquors are gained simultaneously in a pulp mill recovery furnace. Chemically hydrolyzed lignin, called black liquor, is water flushed from the brown pulp stock on a filter surface which permits the liquor and water to drain from the brown stock while the fibers are supported and retained on the filter.

As washed from the brown stock, black liquor contains approximately 10% to 20% solids in solution and suspension with water. To recover the heat and chemical values present in black liquor, the solids concentration of the solution must be increased to approximately 60%: sufficient to fuel a sustained combustion. This is normally accomplished by evaporation. The 60% solids heavy black liquor is burned in the recovery furnace to release both inorganic chemical values combined therewith and heat for steam generation. A portion of such liquor generated steam is used in a continuous evaporation flow stream for black liquor concentration with the remainder used in support of other mill processes such as paper drying.

This interrelated chemical recovery process is economically dependent on the balance between heat value and water in the black liquor flow stream. Excess water in the liquor stream adds to the heat demand for liquor evaporation thereby reducing the quantity of heat available from lignin fuel to support other mill processes. Such other mill processes must consequently be supported by purchased, supplemental fuels thereby adding dramatically to the overall mill energy costs.

The usual source of such excess liquor water is at the pulp washers, the first objective of most pulp mills being a clean pulp. Excess lignin remaining in the brown stock beyond the washers adds to the bleaching chemical costs or finally, in unacceptable paper quality.

From the foregoing, it should be appreciated that pulp washing efficiency is pivotal to the favorable economics of a pulp mill.

In terms of operating costs, the brown stock washing system presents a trade-off between the costs associated with dissolved solids carryover and the amount of wash water needed to achieve that level of solids carryover. The costs associated with solids carryover are, (1) Chemical makeup needed for cooking liquor, (2) Chemical demand in the chlorination bleaching stage caused by dissolved solids in the liquor, and (3) Heat value of the lost solids which would have been burned in the recovery boiler. Wash water usage costs directly determine steam costs in the evaporators. Reducing the amount of wash water used increases the solids carryover and vice versa and there is an optimum operating condition that minimizes the above costs. Continuously monitoring the levels of dissolved solids carryover from the washing system and adjusting the wash water usage is the most effective way to operate economically.

The present state of the art includes several techniques for monitoring the quantity of dissolved solids remaining in a particular brown stock product. One such technique is an estimation of pulp mat dissolved solids levels by differential inference. Hydrometric devices measure the specific gravity of filtrate to the evaporators. From specific gravity, solids content of the washer filtrate is inferred. By assuming an average quantity of dissolved solids originally present in the brown stock, the inferred value of solids removed with the filtrate is deducted from the assumed original value to conclude the quantity of dissolved solids remaining in the brown stock.

The above state-of-the-art technique does not accurately measure the level of solids carryover from the washer for two primary reasons. First, there is a substantial time difference between the moment filtrate is drawn from a particular flow increment of brown stock and the moment the respective filtrate flow increment is hydrometrically measured for solids percentage. Secondly, the hydrometric data on evaporator entry solids is highly distorted by large quantities of dilution water whereby a very small decrease in the percentage of solids to the evaporators represents a very large increase in solids carryover in the brown stock.

Another technique for determination of the dissolved solids concentration remaining in washed brown stock is by measuring electrical conductivity in the final washer filtrate. Since conductivity of the filtrate indicates the concentration of dissolved solids therein, by differential inferrence the dissolved solids carryover is deduced. J. R. Lavigne, An Introduction to Paper Industry Instrumentation, pg. 344, Miller Freeman Publication, San Francisco, Calif., 1972. See also R. V. Gossage and J. M. McSweeney, Correlation of Solids and Soda Content with Conductivity in Brown Stock Washer Systems, TAPPI Vol. 60, No. 4, Apr., 1977 pg. 110.

Electrical conductivity of mat liquor has also been used for shower water control. In such case a batch sample of pulp mat is taken manually from the flow stream for manual liquor expression therefrom. The liquor so expressed is tested for conductivity and the shower water flow regulated accordingly.

Although it has been known that electrical conductivity of brown stock liquor is related to liquor dissolved solids, the test has heretofore only been applied to relative low consistency, aqueous systems such as the washer drum mixing vat, the washer filtrate or batch samples of mat liquor after manual separation from respective pulp by expression.

An objective of the present invention, therefore, is to provide a continuous and immediate measure of solids carryover in brown stock directly from the pulp mat on the drum filter screen.

Another object of the present invention is to measure the solids carryover in brown stock respective to a particular washer.

A further object of the present invention is to provide a direct and immediate method of evaluating performance quality and efficiency of a particular brown stock washer.

SUMMARY

These and other objects of the invention are accomplished by an electrical circuit that is arranged to include the washer drum filter surface as a ground electrode. Potential source charged electrodes are positioned to contact the surface of a drum carried brown stock mat at a point following the wash showers. An amperage measuring means is connected in circuit between the electric potential source and the charged electrodes to measure current flow across the mat.

At substantially the same point on the mat where current is measured, mat thickness is also measured. Resolving the data of potential value, current value and mat thickness, a quotient is obtained with the unit mat thickness which has been found to have a substantially direct relationship with the relative percentage of dissolved solids found in the mat at the point of current measurement.

BRIEF DESCRIPTION OF THE DRAWING

Relative to the drawing wherein:

FIG. 3 is a graphic representation of the dissolved solids content of a pine pulp mat liquor correlation to the electrical conductivity rate of the mat liquor;

FIG. 4 is a graphic representation of the dissolved solids content of a hardwood pulp mat liquor correlation to the electrical conductivity rate of the mat liquor;

DESCRIPTION OF THE PREFERRED EMBODIMENT

Figure 1:
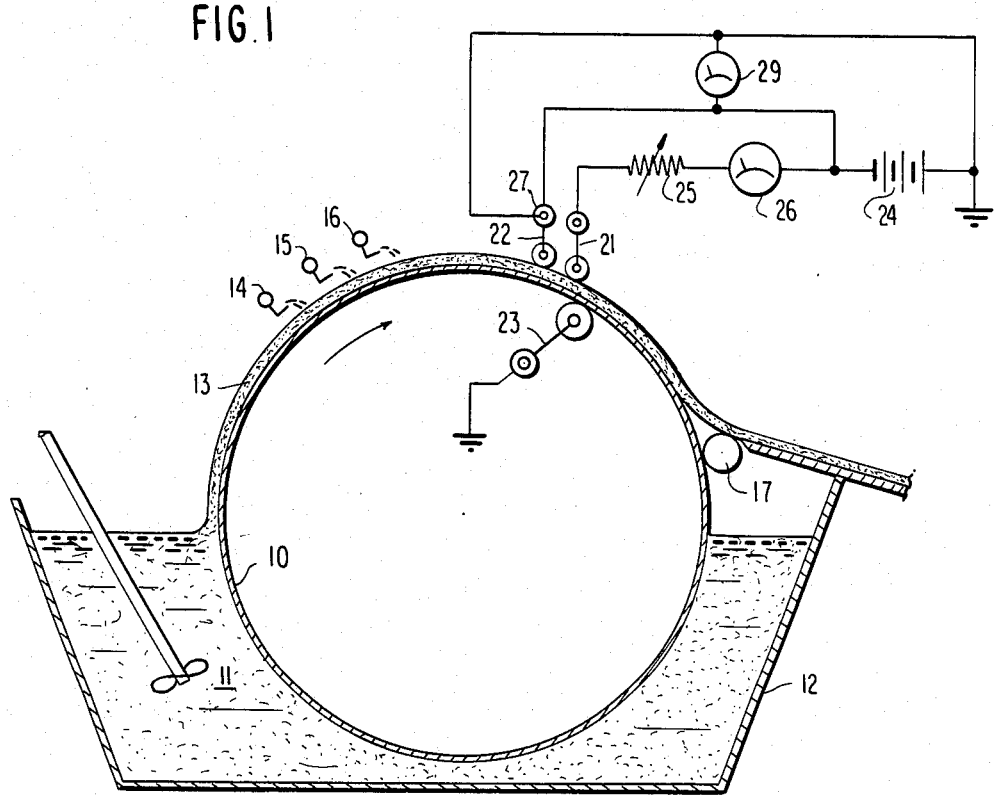
FIG. 1 is a schematic elevation of a paper pulp washing apparatus having the present invention provided therein.

The present invention is generally represented by FIG. 1 which schematically illustrates a rotating drum filter 10 that is partially immersed in an aqueous suspension 11 of brown pulp stock held by a mixing tank 12.

A partial vacuum drawn within the drum 10 interior induces stock flow from the reservoir 11 against the screen surface of the drum which passes as filtrate the aqueous stock medium known as black liquor. In the process, dewatered fibers are retained on the screen surface to accumulate a mat 13 thereof from ¼ to 1 inch in thickness.

As the mat 13 is carried by the drum surface over the first rotational quadrant ascedent from the reservoir 11 surface, a plurality of shower lines 14, 15 and 16 gently distribute wash liquor over the mat surface to induce undiffused or plug flow displacement of the original black liquor remaining in the mat interstices.

Although undiffused displacement of interstitial mat liquor is the objective of the aforedescribed wash procedure and equipment, it is the inherent limitations of the process, in various degrees, to achieve the desired objective that prompts need for the present invention. Numerous closed pores within the mat matrix entrapping corresponding pore space volumes of black liquor are not available to the displacement flow of wash liquor. The degree to which such trapped black liquor remains in the mat matrix after washing defines the overall efficiency of the wash equipment and process conditions. Many of these conditions may be altered during the ongoing process to reduce the number of closed cell pores in the matrix thereby improving the wash efficiency. However, it is not always clear exactly which process variable is in need of corrective alteration. Consequently, the wash process controller needs an immediate and objective report on the relative quantity of black liquor carried over in the mat past the wash liquor showers for corrective action evaluation.

Pursuant to this end, it has been noted that the relative percentage of dissolved solids in a black liquor is directly proportional to the electrical conductivity of the organic solution.

Accordingly, it may be deduced that as black liquor containing dissolved solids is removed from a brown stock mat and replaced with lower solids wash liquor, the electrical conductivity through the washed mat is reduced accordingly.

However, due to variabilities in material flow rates to the washers and other washer operating conditions, the brown stock mat accumulated on a particular drum surface is not always of the same thickness. As the mat thickness changes, so too does the quantity of interstitial liquor held between the mat surface and the drum screen surface: a circumstance that directly affects the absolute conductivity value as measured between the two surfaces.

For a meaningful measurement of mat held liquor solids by the conductivity function, it is therefore necessary to normalize a momentary absolute conductivity measurement by a mat thickness function. It is the specific conductivity, in units such as mhos/cm, of the interstitial liquor that meaningfully describes the relative value of black liquor carryover. To affect that end, it is also necessary to measure the momentary mat thickness simultaneous with measurement of the absolute mat conductivity.

Accordingly, the FIG. 1 embodiment of the present invention provides two roller foot pendants 21 and 22 for contacting the mat 13 surface in the descendant quadrant of the drum circle prior to the point of mat extraction by the doctor roll 17.

A third roller foot pendant or brush 23 is illustrated by the FIG. 1 schematic to represent a reliable ground circuit connection of the drum 10 surface screen although a dedicated ground brush may not always be necessary due to inherent grounding of the drum surface through axle shaft bearing supports not shown.

Pendant 21 is an electrical conductor element in circuit connection with a direct current power source 24, a ballast resistor 25 and an ammeter 26. Pursuant to Ohms law, $I = e/r$, conductance, or its reciprocal, resistance, may be determined from a circuit of known potential, e, and current I. Hence, the absolute value of the mat 13 conductance may be determined from the FIG. 1 circuit data.

Pendant 22, which is positioned adjacent to conductor pendant 21, is connected to a rotary potentiometer 27. The pendant 22 rotative position relative to the drum screen surface is calibrated in terms of variable resistance or voltage across the potentiometer 27 whereby observation of the voltmeter 29 will infer the mat thickness.

Knowing both, the absolute conductance value of the mat and the thickness, the specific conductivity of the mat liquor may be determined.

Figure 2:
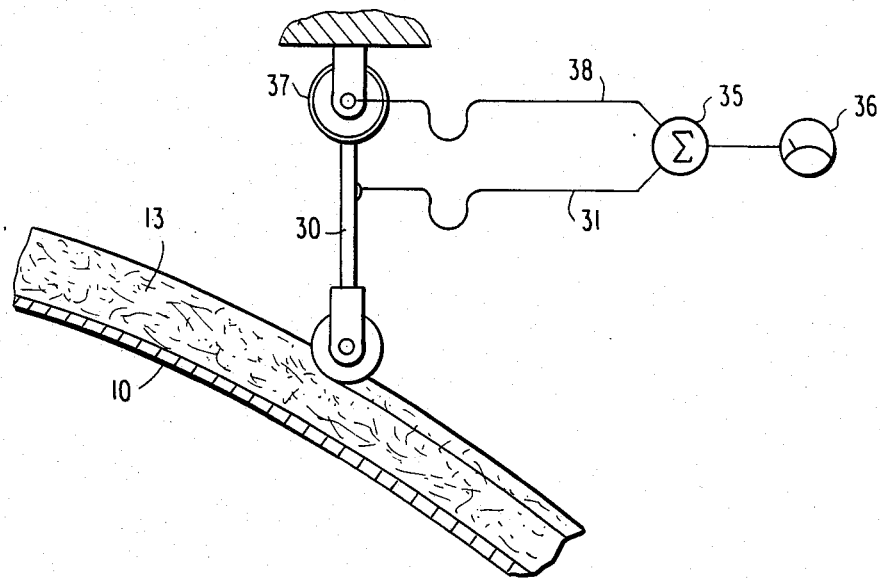
FIG. 2 is an alternative embodiment of the sensory structure of the present invention.

The FIG. 2 embodiment of the invention represents a pendant 20 construction whereby both measurements may be taken with a single apparatus. The pendant shaft is connected to the rotational element of rotary potentiometer 37 for issuance of respective signals 31 and 38 to a summing circuit 35 for automatic signal processing and direct determination of the specific conductivity reported by meter 36.

The graph of FIG. 3 illustrates an experimental application of the invention to pine pulp mats. FIG. 4 illustrates similar data from hardwood pulp mats. Although the dissolved solids/conductivity relationships respective to pine and hardwood are distinctive, the two species demonstrate consistent linearity throughout wide ranges of specific conductivity and dissolved solids content of mat liquor.

The inventions of FIGS. 1 and 2 are constructed to utilize a direct current power source. The FIG. 5 embodiment of the invention is powered by an alternating current power source 44 which permits the use of a rotary variable differential transformer 45 for mat thickness measurement in lieu of a rotary potentiometer. A converter 49 matches the power output of a.c. source 44 to the supply specifications of the differential transformer 45. Such rotary variable differential transformers offer the advantages of greater signal sensitivity and strength per unit of angular displacement and less rotational resistance (friction) as compared to a rotary potentiometer. However, the FIG. 5 alternating current embodiment should include a rectifier and noise filter 47. The resistance values of resistors 41 and 42 are unequal and the values of all resistors 41, 42 and 43 are much greater than the resistance value of the mat 13 which is represented in FIG. 5 as a resistor.

As in the case of the FIG. 2 d.c. embodiment of the invention, the output signal from the transformer 45 representative of the mat 13 thickness is combined by a computer 46 with the mat 13 resistance signal to derive the corresponding specific conductivity signal input to recorder 48.

Figure 5:
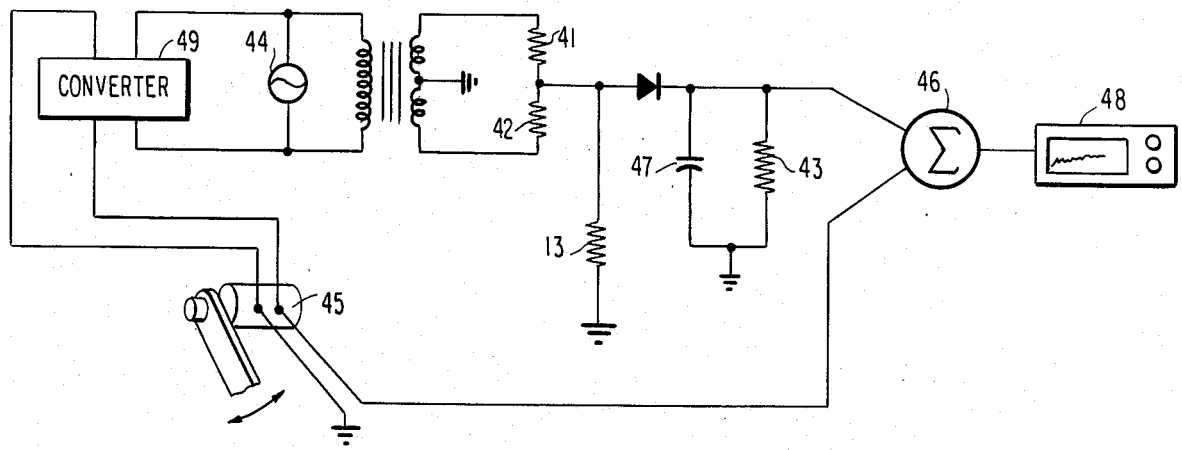
FIG. 5 is an electrical schematic of an alternating current powered embodiment of the invention; and, FIG. 6 is a calibration graph relating voltage readings of the FIG. 5 embodiment recorder 48 to a manually determined quotient L/C where L is the mat thickness and C is the mat conductivity.
Figure 6:
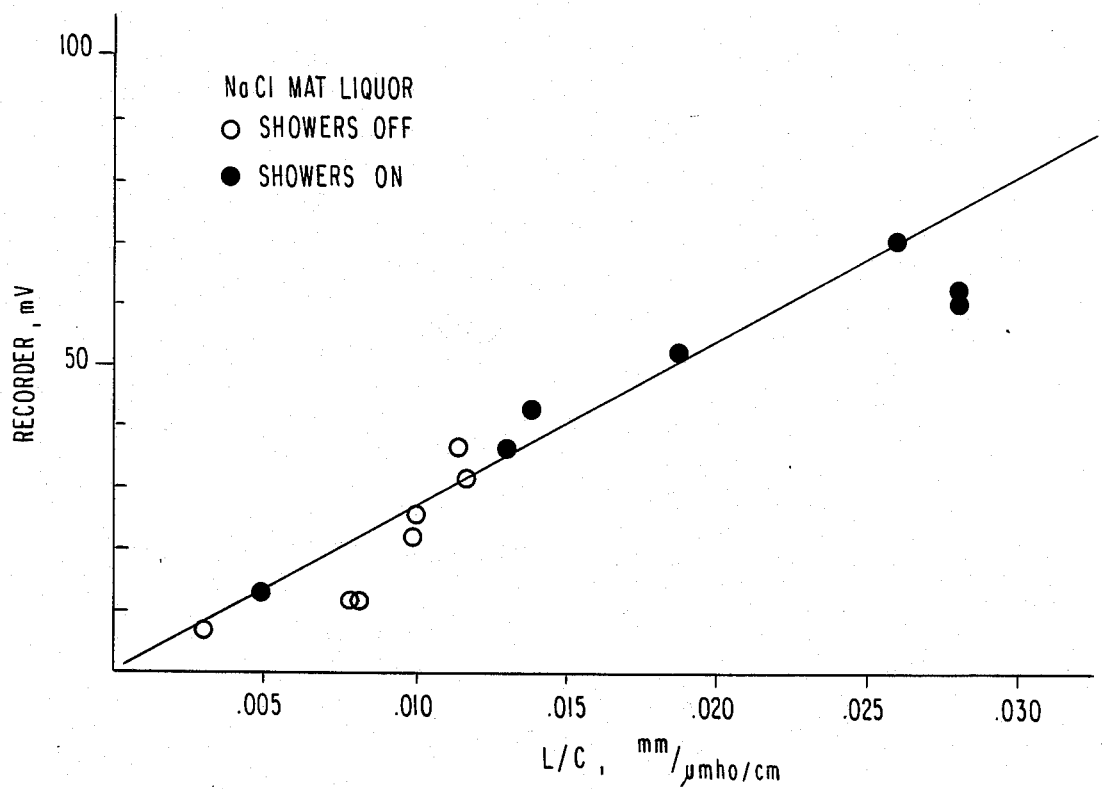

The FIG. 6 graph represents the relationship between voltage readings of the FIG. 5 recorder 48 and the quantity L/C where L is the manually measured mat thickness and C is the manually measured conductivity of in situ mat liquor after manual separation from the mat pulp. The close linear relationship between the invention values and the manually measured values demonstrates the reliability and utility of the invention.

Having fully disclosed our invention and described the presently preferred embodiments thereof,

We claim:

1. A method of monitoring the operational efficiency of brown stock pulp washers comprising the steps of:
   A. Accumulating a wet fibrous mat of pulp on a traveling porous screen from a first aqueous suspension of pulp fiber and black cooking liquor by filter separation of a portion of said black cooking liquor through said screen;
   B. Transporting said wet mat on said screen along a carriage route between a first zone of mat accumulation to a second zone whereat the fiber of said mat is slurried into a second aqueous suspension, said carriage route passing through a third zone located between said first and second zones, whereat wash liquor is applied to said mat to flush additional black cooking liquor therefrom;
   C. First correlating a range of dissolved solids concentration values occurring in the black cooking liquor constituent of said first aqueous suspension to a corresponding range of specific electrical conductivity values respective to said black liquor constituent;
   D. Continuously measuring, in situ, the specific conductivity of said mat along the mat carriage route between said third zone and said second zone; and
   E. Relating said measured specific conductivity to said first correlation for determination of the dissolved solids concentration value remaining in said mat following said wash liquor application.

2. A method of determining the effectiveness of a pulp washing process to remove dissolved solids from the presence of digested paper pulp comprising the steps of:
   A. Developing a first correlation between (1) concentration levels of dissolved solids found in an aqueous solution with which said pulp is mixed and (2) electrical resistance values respective to said aqueous solution dissolved solids concentration levels;
   B. Developing a fibrous mat from said pulp mixture for carriage along an increment of a traveling, filter screen circuit of said washing apparatus, said mat being supported on a surface of said screen along said travel increment;
   C. Distributing wash liquor onto the surface of said screen supported mat at a fixed position along said circuit increment for partial displacement of dissolved solids containing aqueous solution retained within interstitial pores of said mat, said fixed position being located between a first zone of mat development and a second zone of mat dispersal;
   D. Continuously measuring the specific resistance of said mat, in situ, between said mat surface and said carriage screen surface at a point along said circuit increment between said fixed position of wash liquor distribution and said second zone of mat dispersal; and
   E. Relating said measured specific resistance to said first correlation for determination of the dissolved solids concentration level remaining in said interstitial pores of said mat.

3. A method of monitoring pulp washer efficiency as described by claim 2 wherein said specific resistance measurement comprises a direct, absolute measurement of electrical resistance between said mat and carriage screen surfaces that is normalized by a linear measurement of the distance between said surfaces.

* * * * *